United States Patent
Sakai et al.

(10) Patent No.: US 12,350,280 B2
(45) Date of Patent: Jul. 8, 2025

(54) PHARMACEUTICAL COMPOSITION

(71) Applicants: Mari Sakai, Tokyo (JP); ELYSIUM SCIENCE CO., LTD., Moriyama (JP)

(72) Inventors: Mari Sakai, Tokyo (JP); Kiyoaki Kawahara, Moriyama (JP); Kazuya Kawahara, Moriyama (JP)

(73) Assignees: Mari Sakai, Tokyo (JP); Elysium Science Co., Ltd., Moriyama (JP)

( * ) Notice: Subject to any disclaimer, the term of this patent is extended or adjusted under 35 U.S.C. 154(b) by 0 days.

(21) Appl. No.: 18/687,295

(22) PCT Filed: Mar. 24, 2023

(86) PCT No.: PCT/JP2023/012050
§ 371 (c)(1),
(2) Date: Feb. 27, 2024

(87) PCT Pub. No.: WO2023/182529
PCT Pub. Date: Sep. 28, 2023

(65) Prior Publication Data
US 2024/0316080 A1 Sep. 26, 2024

(30) Foreign Application Priority Data
Mar. 25, 2022 (JP) .................... 2022-050641

(51) Int. Cl.
*A61K 31/675* (2006.01)
*A61K 9/00* (2006.01)
*A61K 31/201* (2006.01)
*A61K 31/726* (2006.01)
*A61K 45/06* (2006.01)

(52) U.S. Cl.
CPC .......... *A61K 31/675* (2013.01); *A61K 9/0019* (2013.01); *A61K 31/201* (2013.01); *A61K 31/726* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2005/0208124 A1* | 9/2005 | Araki | A61P 29/00 514/250 |
| 2006/0116328 A1* | 6/2006 | Babizhayev | A61Q 19/04 514/400 |
| 2006/0205633 A1* | 9/2006 | Nishitani | A61K 45/06 514/17.7 |
| 2011/0124577 A1* | 5/2011 | Taimatsu | A23L 27/86 426/536 |
| 2015/0011500 A1* | 1/2015 | Dake | A61P 25/28 514/54 |
| 2018/0228824 A1 | 8/2018 | Yoshino et al. | |
| 2020/0016183 A1 | 1/2020 | Shinzato et al. | |
| 2020/0222351 A1* | 7/2020 | Dhamane | A61K 31/192 |
| 2020/0268632 A1 | 8/2020 | Tanaka et al. | |
| 2021/0169991 A1* | 6/2021 | Nakamura | A61P 35/00 |
| 2021/0188905 A1 | 6/2021 | Sallam et al. | |
| 2022/0031596 A1 | 2/2022 | Tanaka et al. | |
| 2023/0117757 A1 | 4/2023 | Megumi et al. | |

FOREIGN PATENT DOCUMENTS

| | | |
|---|---|---|
| CN | 109350653 A | 2/2019 |
| CN | 110338412 A | 10/2019 |
| CN | 115590204 A | 1/2023 |
| JP | 2007197363 A | 8/2007 |
| JP | 2011084516 A | 4/2011 |
| JP | 2011201875 | 10/2011 |
| JP | 2017002015 A | 1/2017 |
| JP | 2018002604 A | 1/2018 |
| JP | 2018121583 A | 8/2018 |
| JP | 2018131418 | 8/2018 |
| JP | 2018203639 A | 12/2018 |
| JP | 2021113169 A | 8/2021 |
| JP | 2021532800 A | 12/2021 |
| WO | WO 2018147385 A1 | 8/2018 |
| WO | WO 2019054485 | 3/2019 |

(Continued)

OTHER PUBLICATIONS

Holecek, M., Branched-chain amino acids in health and disease; metabolism, alterations in blood plasma, and as supplements, Nutrition & Metabolism, 2018, 15:33.

(Continued)

*Primary Examiner* — Dale R Miller
(74) *Attorney, Agent, or Firm* — The Harris Firm

(57) ABSTRACT

[Problem] To provide a pharmaceutical composition that is effective against diseases caused by immune abnormalities. [Solution] The pharmaceutical composition of the present invention comprises chondroitin sulfate, unsaturated fatty acid, vitamin B, and nicotinamide mononucleotide, and can be adjusted in a way to normalize immune abnormalities. Preferably, the aforementioned vitamin B is vitamin $B_2$, vitamin $B_6$ and vitamin $B_{12}$, and more preferably, the aforementioned vitamin $B_2$ is flavin mononucleotide. Moreover, it is preferable that the composition of the present invention further comprises an amino acid. More preferably, the amino acid is at least one branched chain amino acid selected from valine, leucine and isoleucine.

6 Claims, 1 Drawing Sheet

(56) References Cited

FOREIGN PATENT DOCUMENTS

WO     WO 2020054795     3/2020
WO     WO 2021187396 A1     9/2021

OTHER PUBLICATIONS

Sakurai, K et al., Consumption of Oleic Acid on the Preservation of Cognitive Functions in Japanese Elderly Individuals, Nutrients, 2021, vol. 13, 284 (pp. 1-10).
ISA, International Search Report (ISR) relating to International Application No. PCT/JP2023/012050, dated May 16, 2023.
ISA, Written Opinion of the ISA relating to International Application No. PCT/JP2023/012050, dated May 16, 2023.
JPO, Office Action of Application Ser. No. JP2022050641A, dated Jun. 8, 2022.

* cited by examiner (a)
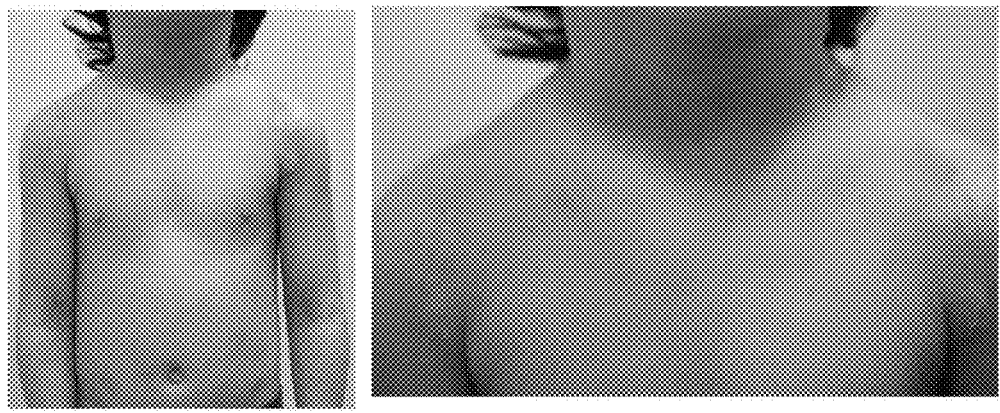
(b)
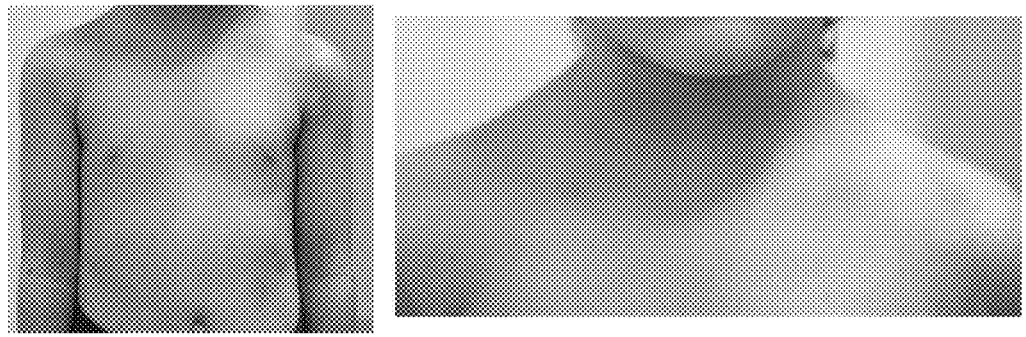

PHARMACEUTICAL COMPOSITION

CROSS REFERENCE TO PRIOR APPLICATION(S)

This application is a U.S. National Stage Patent Application of PCT International Patent Application Ser. No. PCT/JP2023/012050 (filed on Mar. 24, 2023) under 35 U.S.C. § 371, which claims priority of Japanese application Ser. No. JP2022-050641 (filed on Mar. 25, 2022) under 35 U.S.C. § 119, the entire contents of all of which are hereby incorporated herein by reference.

TECHNICAL FIELD

The present invention relates to a pharmaceutical composition, and particularly to a pharmaceutical composition that can normalize immune abnormalities and/or improve brain function, etc.

BACKGROUND

Macrophages are a type of white blood cell, and are cells with phagocytic capacity that are expressed and migrate in various organs such as the brain and liver. The phagocytosis of these macrophages is activated by cytokines, which are low-molecular weight proteins secreted from T cells, and they attack foreign substances that have invaded the body and denatured substances that have been produced within the body.

On the other hand, it has been pointed out that due to overexpression of proteins, macrophages may be activated excessively and cause excessive inflammatory reactions, which may lead to various diseases such as arthritis and allergies.

As a countermeasure for such cases, Patent Document 1 discloses an anti-inflammatory agent containing macrophage migration inhibitory factor (MIF) that aims to suppress the occurrence of inflammatory diseases.

PRIOR ART DOCUMENT

Patent Document

[Patent Document 1] Japanese Unexamined Patent Application Publication No. 2011-201875

SUMMARY OF INVENTION

Problem to be Solved by Invention

The inventors have focused on the effect of macrophage activation, and have conducted research aimed at improving infertility by utilizing the activation effect of macrophages or the activation effect of mitochondria. As a result, they discovered a combination of ingredients that is effective against diseases caused by immune abnormalities, such as terminal cancer, atopic dermatitis, allergies, and the sequelae, etc. of viral infections, as well as brain function.

The present invention has been made in view of the above circumstances, and an object of the present invention is to provide a pharmaceutical composition that is effective against diseases, etc. caused by immune abnormalities.

Means to Solve Problem

The pharmaceutical composition according to the present invention for achieving the above object comprises chondroitin sulfate, unsaturated fatty acid, vitamin B group, and nicotinamide mononucleotide, and is adjusted to normalize immune abnormalities.

That is, through interaction between the components contained in the pharmaceutical composition, cell traits can be controlled while suppressing excessive activation of specific cells. In particular, it was found that the pharmaceutical composition of the present invention may normalize immune abnormalities and improve brain function etc. as a result of the combination of vitamin B and nicotinamide mononucleotide with the basic components of chondroitin sulfate and unsaturated fatty acid.

Furthermore, it exhibits physiological effects such as promoting the synthesis of hemoglobin and the biosynthesis of proteins and nucleic acids, while having anti-arteriosclerotic, antioxidant, or anti-inflammatory effects.

Furthermore, it is possible to control cell proliferation, cell differentiation, and induction of cell death, as well as control cells that may cause immune abnormalities, such as cells related to biological defense and inflammation.

Therefore, by controlling cell traits to normalize immune abnormalities, the composition would be effective for regulating immunity, which can be used to treat diseases such as cancer, atopic dermatitis, allergies, sequelae of viral infections, and diseases caused by immune abnormalities.

In particular, since the composition comprises nicotinamide mononucleotide (NMN), it can be expected to have a significant effect on diseases caused by immune abnormalities by activating sirtuin genes.

The B vitamins contained in the composition may be vitamin $B_2$, vitamin $B_6$ and vitamin $B_{12}$, with vitamin $B_2$ being particularly preferably flavin mononucleotide (FMN).

The composition further comprises an amino acid, and the amino acid is preferably at least one branched chain amino acid selected from valine, leucine, and isoleucine.

The composition may further comprise L-carnosine.

The chondroitin sulfate contained in the composition may be chondroitin sulfate A and chondroitin sulfate C, and chondroitin sulfate C is preferably derived from the cartilage of aquatic organisms.

On the other hand, the unsaturated fatty acid contained in the composition is preferably oleic acid.

Effect of Invention

According to the present invention, the composition is effective against diseases caused by immune abnormalities.

BRIEF DESCRIPTION OF DRAWINGS

FIG. 1(a) shows the condition of the skin of a boy with atopic dermatitis before the start of administration of the composition of the present invention, and FIG. 1(b) shows the condition of his skin after the start of administration.

DETAILED DESCRIPTION

Next, a composition according to an embodiment of the present invention will be explained.

The composition may be taken orally in the form of a tablet or capsule, or may be applied to the target area, or may be used as an injectable liquid or introduced into the body as an infusion, but in this embodiment, it is particularly preferable that the composition be introduced into the body as an infusion.

In this embodiment, the composition comprises chondroitin sulfate, unsaturated fatty acid, vitamin B, and nicotinamide mononucleotide (NMN), and is adjusted to normalize immune abnormalities and improve brain function, etc. The composition of the present invention may further comprise vitamin D, a branched chain amino acid, and/or carnosine.

In the present invention, an immune abnormality refers to a response that deviates from a normal immune response. Therefore, an abnormality in immunity refers to an excessive immune response in general. For example, when infected with a virus, an inflammatory response is induced, resulting in symptoms such as fever, pain, and fatigue. Although these are normal immune responses, if they continue for a long period of time they will exhaust the patient's physical strength. In particular, fatigue and pain impair the patient's QOL and do not contribute to the protective response against viruses, so they can be considered as immune abnormalities. The composition of the present invention, which works to normalize immune abnormalities, can be used to reduce fatigue or increase vitality.

In this embodiment, diseases caused by immune abnormalities to which the composition is applied include, for example, terminal cancer, atopic dermatitis, allergies, and the sequelae, etc. of viral infections. In particular, it is also effective for conditions such as atopic dermatitis and allergies for which there were no treatments or therapeutic drugs previously.

Furthermore, it also applies to diseases caused by excessive activation of macrophages, such as chronic rheumatoid arthritis, delayed-onset allergies, arteriosclerosis, endometriosis, acute respiratory distress syndrome, bronchitis, acute myocardial infarction, diabetes, and sepsis, etc. due to infection.

Chondroitin sulfate contained in the composition is a mucopolysaccharide classified as a group of sulfated glycosaminoglycans, and is widely distributed in all tissues such as connective tissues and mucus, etc. in the body of animals (organisms). Chondroitin sulfate may be blended in the composition of the present invention in amounts of 1.0-10.0% by mass. Chondroitin sulfate is blended in the composition of the present invention in amounts of 1.0% or more by mass preferably, and in amounts of 2.2% or more by mass more preferably. Furthermore, chondroitin sulfate is blended in the composition of the present invention in amounts of 8.0% or less by mass preferably, and in amounts of 6.0% or less by mass or 5.0% or less by mass more preferably.

This chondroitin sulfate exists as a proteoglycan covalently bonded to a protein, and includes chondroitin sulfate A, which has a sulfate group attached to the 4-position of N-acetylgalactosamine, chondroitin sulfate B, which consists of iduronic acid and N-acetylgalactosamine, which has a sulfate group attached to the 4-position, and chondroitin sulfate C, which has sulfate group bound to the 6-position of N-acetylgalactosamine.

Other types of chondroitin sulfate include chondroitin sulfate D and chondroitin sulfate E, which have two sulfate groups attached.

In this embodiment, chondroitin sulfate A and chondroitin sulfate C, which are often derived from the cartilage of aquatic organisms, are preferably used.

The type of aquatic organism to be used is not limited, and may be fish, mammals, or molluscs, and the range of possible organisms include whales, rays, sharks, sturgeon, salmon, or squid, etc., but in practical terms, shark cartilage is particularly preferred as a method to quantitatively measure chondroitin sulfate C that is extracted from it has been established.

Note that the cartilage is not limited to that from aquatic organisms, and cartilage of terrestrial organisms may also be used. Examples of terrestrial organisms include mammals such as cows and pigs.

This chondroitin sulfate has the property of controlling cell traits such as cell adhesion, cell migration, differentiation, and proliferation, so for example, it can help produce nitric oxide, which kills cancer cells, without inducing excessive activation of macrophages due to cytokine production.

Unsaturated fatty acids are fatty acids with one or more unsaturated carbon bonds. Naturally occurring unsaturated fatty acids have one or more double bonds and are substituted for saturated fatty acids in fats, thereby imparting changes in fat properties. Unsaturated fatty acid may be blended in the composition of the present invention in amounts of 0.5 to 5.0% by mass. Unsaturated fatty acid may be blended in the composition of the present invention in amounts of 1.0% or more by mass preferably, and in amounts of 1.5% or more by mass more preferably. Moreover, unsaturated fatty acid may be blended in the composition of the present invention in amounts of 5.0% or less by mass preferably, and in amounts of 4.0% or less by mass or 3.0% or less by mass more preferably.

Unsaturated fatty acids include essential fatty acids necessary for the human body, and essential fatty acids include linoleic acid, linolenic acid, and arachidonic acid, and since these cannot be synthesized in the body, they need to be ingested from food.

Furthermore, examples of unsaturated fatty acids include palmitoleic acid and oleic acid.

Linoleic acid is a diunsaturated fatty acid with 18 carbon atoms that is found in many vegetable oils, especially semi-drying oils, and linolenic acid is found in drying oils such as linseed oil and it is a triunsaturated fatty acid with 18 carbon atoms. Arachidonic acid is a tetraunsaturated fatty acid with 20 carbon atoms and is contained in animal visceral fat (brain, liver, kidney, lung, and spleen).

On the other hand, palmitoleic acid is contained in cod liver oil, sardine oil, herring oil, etc., and is a monounsaturated fatty acid with 16 carbon atoms, and oleic acid is a monounsaturated fatty acid with 18 carbon atoms.

As the unsaturated fatty acid in this embodiment, it is most preferable to use oleic acid.

Oleic acid is contained in large amounts in seeds such as olives, avocados, and nuts, and in vegetable oils such as olive oil, safflower oil, and sunflower oil. In this embodiment, it is preferable to use vegetable oils derived from olive oil, and especially preferable to use olive oil (referred to as "extra virgin olive oil") that satisfies certain standards in terms of fragrance, ingredients, etc.

Since this oleic acid has anti-arteriosclerotic, antioxidant, or anti-inflammatory effects, it is expected to particularly suppress the onset or progression of heart disease and cancer.

Vitamin B is a group consisting of vitamin $B_1$, vitamin $B_2$, niacin, pantothenic acid, vitamin $B_6$, vitamin $B_{12}$, folic acid, and biotin, and in this embodiment, vitamin $B_2$, vitamin $B_6$ and vitamin $B_{12}$ are preferably selected. Vitamin B is blended in the composition of the present invention in amounts of 0.1% by mass to 8.0% by mass. It is blended in amounts of 0.5% or more by mass preferably, and in amounts of 4.0% or more by mass more preferably. In addition, vitamin B is blended in the composition of the present invention in amounts of 6.0% or less by mass preferably, and in amounts of 4.0% or less by mass or 2.0% or less by mass more preferably.

Vitamin $B_2$ is a water-soluble vitamin that mainly maintains the functions of the skin and mucous membranes. When ingested into the body, it is converted into flavin mononucleotide (FMN) and flavin adenine dinucleotide (FAD). However, in the body it mainly exists as flavin adenine dinucleotide (FAD).

Flavin mononucleotide (FMN) is a prosthetic group of oxidoreductases including NADH dehydrogenase, and is a compound synthesized from vitamin $B_2$ (riboflavin) by riboflavin kinase. In this embodiment, flavin mononucleotide (FMN) is preferably selected.

Since flavin mononucleotide (FMN) is thought to promote brain activation and to act effectively against diseases of the nervous system, considering the fact that vitamin $B_2$ ingested by the body is mainly converted to flavin adenine dinucleotide (FAD), it is preferable that it is supplemented externally in the form of flavin mononucleotide (FMN).

Compounds with vitamin $B_6$ activity include pyridoxal, pyridoxine and pyridoxamine. Vitamin $B_6$ functions as a coenzyme that supports many amino acids, and plays a role in physiological functions such as normalizing immune function, increasing skin resistance, synthesizing hemoglobin in red blood cells, and synthesizing neurotransmitters.

On the other hand, compounds having vitamin $B_{12}$ activity include adenosylcobalamin, methylcobalamin, hydroxycobalamin, and cyanocobalamin. Such vitamin $B_{12}$ functions as a coenzyme that assists in the biosynthesis of proteins and nucleic acids, or the metabolism of amino acids and fatty acids, and produces or matures red blood cells.

Vitamin D is a general term for vitamin $D_2$ (ergocalciferol) and vitamin $D_3$ (cholecalciferol), and is a type of essential nutrient classified as a fat-soluble vitamin. Vitamin D is blended in the composition of the present invention in amounts of 0.1% by mass to 5.0% by mass. Vitamin D is blended in the composition of the present invention in amounts of 0.5% or more by mass preferably, and in amounts of 1.0% or more by mass more preferably. Furthermore, vitamin D is blended in the composition of the present invention in amounts of 4.0% or less by mass preferably, and in amounts of 2.0% or less by mass more preferably.

While this vitamin D is produced in the body by ultraviolet rays, vitamin $D_2$ is found in plants, especially provitamin $D_2$, which is a precursor of vitamin $D_2$, in shiitake mushrooms, and vitamin $D_3$ is found in large amounts in the liver of fish, so they can also be taken into the body by ingesting them.

Vitamin D has physiological effects such as bone formation and regulation of blood calcium concentration, as well as controlling cell proliferation, cell differentiation, or inducing cell death, as vitamin D expression has been observed in almost all tissues in the body.

Furthermore, vitamin D has also been observed to be expressed in cells related to biological defense and inflammation, such as monocytes, macrophages, antigen-presenting cells, and activated T cells, and thus plays a physiological role in regulating cells that may cause immune abnormalities.

By the way, sirtuin genes have attracted attention as anti-aging and longevity genes in anti-aging research, and the inventors have found that nicotinamide mononucleotides are sirtuin genes that also have efficacy in diseases caused by immune abnormalities.

Nicotinamide mononucleotide is a precursor of nicotinamide adenine dinucleotide ($NAD^+$), which exists naturally in the body and activates the sirtuin gene that inhibits aging. It has attracted much attention in recent years as an anti-aging substance that can substantially supplement nicotinamide adenine dinucleotide ($NAD^+$), which declines with age and is difficult to be supplemented directly externally.

Nicotinamide mononucleotide can be ingested from foods such as edamame, broccoli, avocado, and other vegetables and fruits, but its content in foods is not very high to begin with, and the ability to synthesize nicotinamide mononucleotide in the body declines with age, so supplementation from outside is considered effective.

The content of this nicotinamide mononucleotide in the composition of this embodiment is not particularly limited and is set accordingly. As an example, nicotinamide mononucleotide is blended in the composition of the present invention in amounts of 0.1% by mass to 5.0% by mass. Nicotinamide mononucleotide is blended in the composition of the present invention in amounts of 0.5% or more by mass preferably, and in amounts of 1.0% or more by mass more preferably. Furthermore, nicotinamide mononucleotide is blended in the composition of the present invention in amounts of 4.0% or less by mass preferably, and in amounts of 2.0% or less by mass more preferably.

When nicotinamide mononucleotide is used as the active ingredient of the composition of this embodiment, the sirtuin gene is activated, and the functions such as repairing DNA damaged by aging, improving mitochondrial functions in various organs, regulating energy metabolism, and regulating cell division are demonstrated. This is expected to have a significant effect on diseases caused by abnormalities in the immune system.

The amino acid is a free amino acid having a branched structure in its side chain, and is at least one branched chain amino acid selected from valine, leucine, and isoleucine. In this embodiment, it is preferable that all of valine, leucine, and isoleucine are included. The inclusion of branched chain amino acids in the composition of this embodiment will suppress muscle decomposition and increase muscle mass. In particular, since leucine has the effect of promoting protein synthesis in the body, it promotes the decomposition of suitable amino acids.

This branched chain amino acid is considered to be an essential amino acid for humans, but since it cannot be synthesized within the body, it is considered effective to supplement it externally.

The content of this branched chain amino acid in the composition of this embodiment is not particularly limited and is set accordingly, and the content ratio of each of valine, leucine, and isoleucine when all are included is also particularly not limited, but in the present embodiment, the content ratio of valine:leucine:isoleucine is preferably 1:2:1.

Carnosine is a dipeptide consisting of β-alanine and histidine, and depending on the three-dimensional structure of histidine, L-form and D-form exist. Naturally derived carnosine is L-carnosine, and in this embodiment, L-carnosine (hereinafter simply referred to as "carnosine") is preferably used.

Chondroitin sulfate and unsaturated fatty acid are blended in the composition of the present invention in mass ratios of 4.0:1.0 to 1.5:1.0. Chondroitin sulfate and vitamin B are blended in mass ratios of 8.0:1.0 to 3.0:1.0. Chondroitin sulfate and vitamin D are blended in mass ratios of 8.0:1.0 to 3.0:1.0. Chondroitin sulfate and nicotinamide mononucleotide are blended in mass ratios of 8.0:1.0 to 3.0:1.0. Unsaturated fatty acid and vitamin B are blended in mass ratios of 5.0:1.0 to 2.0:1.0. Unsaturated fatty acid and vitamin D are blended in mass ratios of 5.0:1.0 to 2.0:1.0. Unsaturated fatty acid and nicotinamide mononucleotide are blended in mass ratios of 5.0:1.0 to 2.0:1.0. Vitamin B and vitamin D are blended in mass ratios of 2.0:1.0 to 0.5:1.0. Vitamin B and nicotinamide mononucleotide are blended in mass ratios of 2.0:1.0 to 0.5:1.0. Vitamin D and nicotinamide mononucleotide are blended in mass ratios of 2.0:1.0 to 0.5:1.0.

Inclusion of carnosine in the composition of this embodiment is expected to further exhibit effects such as promotion of skin metabolism, regulation of autonomic nerve actions, alleviation of stress, improvement of learning function, and anti-anxiety effects.

The composition thus comprises chondroitin sulfate, unsaturated fatty acid, B vitamins (flavin mononucleotides, vitamin $B_6$ and vitamin $B_{12}$), optional vitamin D, nicotinamide mononucleotide, optional branched chain amino acid and optional carnosine. The interaction of these components with each other allow to control cell traits while suppressing excessive activation of any cells such as macrophages.

Furthermore, it exhibits physiological effects such as promoting the synthesis of hemoglobin and the biosynthesis of proteins and nucleic acids, while having anti-arteriosclerotic, antioxidant, or anti-inflammatory effects.

Furthermore, it is possible to control cell proliferation, cell differentiation, and induction of cell death, as well as control cells that may cause immune abnormalities, such as cells related to biological defense and inflammation.

Therefore, by controlling cell traits to normalize immune abnormalities, it can regulate immunity and thus has efficacy in diseases caused by immune abnormalities, such as cancer, atopy, allergies, sequelae of viral infections, chronic rheumatoid arthritis, delayed-onset allergies, arteriosclerosis, endometriosis, acute respiratory urgency syndrome, bronchitis, acute myocardial infarction, diabetes, sepsis due to infection, etc.

Specifically, for example, in the case of terminal cancer, it can delay the progression of cancer and prolong life, while preventing atopy and allergies, promoting healing of atopy and allergies, alleviating sequelae of viral infections, etc.

In particular, since the composition of this embodiment comprises nicotinamide mononucleotide, it can be expected to have a significant effect on diseases caused by immune abnormalities by activating sirtuin genes.

The composition of the present invention may be a composition for infusion, in which case it may further include a well-known infusion solution. Furthermore, the composition of the present invention may be a composition for injection, or may be orally ingested in the form of a tablet, capsule, etc. Depending on the dosage form, a well-known liquid or a solid medium may further be included.

The composition of the present invention can be used after being diluted in a medium such as an infusion solution or physiological saline. In this case, the amount of each active ingredient described herein as "% by mass" shall be read as "parts by mass". The total amount of the remaining medium other than each active ingredient of the composition of the present invention and the diluting medium is 10 parts by mass or more, 20 parts by mass or more, 50 parts by mass, 100 parts by mass, 500 parts by mass, 1,000 parts by mass, 5,000 parts by mass or more based on 1 part by mass of chondroitin sulfate, or may even be 50,000 parts by mass or less, 10,000 parts by mass or less, 5,000 parts by mass or less, 1,000 parts by mass or less, or 500 parts by mass or less.

As an example, the composition of the present invention comprises 1.0 to 6.0 parts by mass of chondroitin sulfate, 0.5 to 5.0 parts by mass of oleic acid, 0.5 to 4.0 parts by mass of flavin mononucleotide, 0.5 to 4.0 parts by mass of nicotinamide mononucleotide and 10 to 50,000 parts by mass (preferably 100 to 10,000 parts by mass or less) of a medium.

EXAMPLES

Next, the present invention will be explained by examples.

A study was conducted wherein 13 subjects mainly in their 30s and 40s (6 men, 7 women) were physically examined after the use of the composition of Example 1 containing 5% by mass of chondroitin sulfate, 3% by mass of oleic acid, 1% by mass of flavin mononucleotide, 1% by mass of vitamin D, 1% by mass of nicotinamide mononucleotide, and the remainder as infusion solution for drip infusion.

In the study of this example, the composition was in the form of an infusion solution, and a method was adopted in which the composition containing physiological saline was administered to the subjects as an infusion solution by drip infusion.

All subjects were infected with mild or moderate novel coronavirus infection (COVID-19), and the study in this example was carried out with the objective of evaluating the effect of the above composition on infection.

The subjects exhibited typical symptoms of COVID-19, such as loss of taste, loss of smell, fever, and fatigue, and when the changes in these symptoms were evaluated before and after administration of the composition, all subjects tended to feel less fatigued and increased vitality immediately after administration of the composition.

On the other hand, although symptoms of fever were observed in some subjects, this fever was considered to be a temporary symptom caused by the action of nicotinamide mononucleotide.

Although trends in reduced fatigue and improved vitality due to administration of the composition continued for 3 days, symptoms of fatigue were observed again afterwards. That is, at present, it is thought that the duration of action after administering the composition is about 3 days, but by repeating the administration of the composition again after 3 days, the duration of action is thought to gradually improve (prolong).

In the study of this example, the composition was administered as an infusion solution by intravenous drip, but it could also be administered as an injectable liquid or taken orally in tablet or capsule form, and even if it is administered in these ways, the same evaluations as in the present example may be made with these methods.

Further, as Reference Example 1, a composition that was the same as the composition of Example 1 except that it did not comprise vitamin B was prepared. When the composition of Example 1 and Reference Example 1 were administered to patients with various diseases, the following results were obtained.

As a result of administering the composition of Example 1 by drip infusion once a month to a man in his 60s suffering from an intractable disease called cerebrospinal fluid hypovolemia, he was able to stand up on his own when putting on his shoes after the second dose, which was previously impossible for him. In addition, the mentally difficult nature of the patient became calmer, suggesting improvement in brain function. This effect was not obtained with long-term administration of the composition of Reference Example 1, but was achieved after switching to the composition of Example 1.

A man in his 60s who had symptoms of urine leakage and residual urine sensation due to aging and decline in male function was given twice-monthly infusions of the composition of Example 1, and after the second infusion, his symptoms improved dramatically and his male function became normal and healthy. In addition, chronic stiff shoulders and chronic fatigue syndrome were improved. A similar treatment was performed on 10 patients with similar symptoms, and similar effects were achieved. Some patients also reported that their sperm became thicker and their sexual desire improved. When the same procedure was performed on a 62-year-old woman, she reported that her vagina went from dry to moist with increased secretion, and her physical condition improved; moreover, the deep wrinkles at the corners of her eyes disappeared after the fourth treatment.

When three women in their 30s undergoing infertility treatment were given monthly infusions of the composition of Example 1, two became pregnant in the second month, and one became pregnant five months later.

A woman in her 40s with numbness in her hands and feet, dizziness, palpitations, and general malaise due to sequelae of COVID-19 infection was given an infusion of the above composition, and her symptoms improved the next day after a single dose.

Continued monthly infusion of the composition of Example 1 to two women each in their 30s, 40s, and 50s with severe periodontal disease, the gingival swelling and bleeding improved from 3+ to 2+ after the second infusion.

A 30-year-old woman with numerous pimples on her face received one infusion of the composition of Example 1. After one month, the number of pimples was reduced to about one-fourth, inflammation and pigmentation of the pimples were improved, and the skin was whitened and moisturized.

Men and women in their 20s, 30s, 40s, and 60s who continuously received monthly infusions of the composition of Example 1 were negative themselves for COVID-19 despite coming into close contact with an infected person, which suggested they had developed enhanced immunity.

A woman in her 50s who received monthly infusions of the composition of Example 1 for six months reported that her depressive symptoms improved from 5+ to 3+ and that she felt like going out. This suggested improvement in the autonomic nervous system and brain function.

A man in his 60s who received twice-monthly infusions of the composition of Example 1 continuously for six months had his gray hair reduced by about one-fourth and his hair became taut and dark. When a woman in her 40s underwent the same treatment for one year, her gray hair was reduced by about half, and her skin tone and wrinkles improved from 3+ to 1+.

A man in his 60s who continued to receive infusions of the composition of Example 1 twice a month for 8 months had his food allergy improved and his yam allergy eliminated.

An infusion composition was prepared containing 5% by mass of chondroitin sulfate, 3% by mass of oleic acid, 1% by mass of flavin mononucleotide, 1% by mass of vitamin D, 1% by mass of nicotinamide mononucleotide, and the remainder as composition for drip infusion containing water, and 0.3 mL of the composition was added to 100 mL of an infusion solution to manufacture the drip infusion drug.

A boy with atopic dermatitis showed improvement after administering this infusion drug once a week for 3 weeks, so he continued to receive infusions once a month for 6 months, which resulted in dramatic improvement of skin inflammation. FIG. 1(*a*) shows the state before the start of administration of the drip infusion drug, and FIG. 1(*b*) shows the state after the start of administration of the drip infusion drug.

As described above, according to this example, by using the composition specified in the above embodiment, it was possible to normalize the immune abnormalities of subjects. As a result, remarkable effects were observed in all subjects immediately after administering the composition.

The invention claimed is:

1. A pharmaceutical composition for infusion or injection, comprising from 1.0% to 6.0% by mass of chondroitin sulfate, from 0.5% to 5.0% by mass of oleic acid, from 0.5% to 4.0% by mass of flavin mononucleotide, and from 0.5% to 2.0% by mass of nicotinamide mononucleotide, wherein the chondroitin sulfate and the nicotinamide mononucleotide are blended in mass ratios of 8.0:1.0 to 3.0:1.0.

2. The pharmaceutical composition according to claim 1, further comprising an amino acid.

3. The pharmaceutical composition according to claim 2, wherein the amino acid is at least one branched chain amino acid selected from valine, leucine, and isoleucine.

4. The pharmaceutical composition according to claim 1, further comprising L-carnosine.

5. The pharmaceutical composition according to claim 1, wherein the chondroitin sulfate is chondroitin sulfate A and chondroitin sulfate C.

6. The pharmaceutical composition according to claim 5, wherein the chondroitin sulfate C is derived from cartilage of aquatic organisms.

\* \* \* \* \*